(12) United States Patent
Rougeon et al.

(10) Patent No.: US 9,387,260 B2
(45) Date of Patent: *Jul. 12, 2016

(54) VHH ANTIBODIES USED AS PEPTIDE VECTORS FOR DELIVERING A SUBSTANCE OF INTEREST

(75) Inventors: François Rougeon, Sevres (FR); Pierre Lafaye, Malakoff (FR); Jean-Pierre Bourgeois, Saint Mande (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 807 days.

This patent is subject to a terminal disclaimer.

(21) Appl. No.: 12/501,094

(22) Filed: Jul. 10, 2009

(65) Prior Publication Data

US 2010/0021384 A1 Jan. 28, 2010

Related U.S. Application Data

(63) Continuation-in-part of application No. PCT/IB2008/002691, filed on Jun. 26, 2008.

(30) Foreign Application Priority Data

Jun. 29, 2007 (EP) .................................. 07290811

(51) Int. Cl.
*A61K 47/48* (2006.01)
*C07K 16/18* (2006.01)
*A61K 51/10* (2006.01)

(52) U.S. Cl.
CPC ....... *A61K 47/48538* (2013.01); *A61K 51/1018* (2013.01); *C07K 16/18* (2013.01); *A61K 47/48384* (2013.01); *C07K 2317/22* (2013.01); *C07K 2317/569* (2013.01)

(58) Field of Classification Search
CPC .................. C07K 2317/569; C07K 2317/22; A61K 51/1018; A61K 39/0007; A61K 47/48583; A61K 47/48384; A61K 47/48507; A61K 47/48538

See application file for complete search history.

(56) References Cited

U.S. PATENT DOCUMENTS

| | | | |
|---|---|---|---|
| 5,004,697 A * | 4/1991 | Pardridge | 424/1.49 |
| 8,257,705 B2 * | 9/2012 | Tanha | C07K 16/00 424/133.1 |
| 2005/0037421 A1 * | 2/2005 | Honda | C07K 16/00 435/7.1 |
| 2008/0107601 A1 * | 5/2008 | Lauwereys et al. | 424/9.1 |
| 2009/0047300 A1 * | 2/2009 | Abulrob et al. | 424/185.1 |
| 2011/0171720 A1 * | 7/2011 | Muruganandam et al. | 435/235.1 |
| 2011/0200525 A1 * | 8/2011 | Patz et al. | 424/1.11 |

FOREIGN PATENT DOCUMENTS

| WO | WO 02/057445 A1 | 7/2002 |
|---|---|---|
| WO | WO 2004/044204 A2 | 5/2004 |

OTHER PUBLICATIONS

Abulrob 2005 (International Congress Series 1277:212-223).*
van der Linden RHJ et al. Comparison of physical chemical properties of llama VHH antibody fragments and mouse monoclonal antibodies. Biochim Biophys Acta. 1999; 1431:37-46.*
Arbabi-Ghahroudi M et al. (2009) Aggregation-resistant VHs selected by in vitro evolution tend to have disulfide-bonded loops and acidic isoelectric points. Protein Engineering, Design & Selection, 22(2):59-66.*
Machine translation of WO 2004/044204 (Rougeon et al.), provided by EPO Patent Translate, Jul. 2014.*
Chekhonin VP et al. (2005) PEGylated immunoliposomes directed against brain astrocytes. Drug Delivery, 12:1-6.*
Girod et al. (1999) Transport of cationized anti-tetanus Fab'2 fragments across an in vitro blood-brain barrier model: Involvement of the transcytosis pathway. J. Neurochem., 73:2002-2008.*
Li T et al. Cell-penetrating anti-GFAP VHH and corresponding fluorescent fusion protein VHH-GFP spontaneously cross the blood-brain barrier and specifically recognize astrocytes: application to brain imaging. FASEB J. (2012) 26:3969-3979.*
Muruganandam A et al. Selection of phage-displayed llama single-domain antibodies that transmigrate across human blood-brain barrier endothelium. FASEB Journal (Feb. 2002) 16(2), 240-242. Epub Dec. 28, 2001.*
Perruchini C et al. Llama VHH antibody fragments against GFAP: better diffusion in fixed tissues than classical monoclonal antibodies. Acta Neuropathol. (2009) 118:685-695.*
Rissiek B et al. Nanobodies as modulators of inflammation: potential applications for acute brain injury. Frontiers Cell. Neurosci. (2014) 8(344)1-7.*
Abedelnasser Abulrob, et al., "The blood-brain barrier transmigrating single domain antibody: mechanisms of transport and antigenic epitopes in human brain endothelial cells", Journal of Neurochemistry, vol. 95, XP003010699, 2005, pp. 1201-1214.
William M. Pardridge, "Drug and Gene Delivery to the Brain: The Vascular Route", Neuron, vol. 36, Nov. 14, 2002, pp. 555-558.
Ikumi Tamai, et al., "Drug delivery through the blood-brain barrier", Advanced Drug Delivery Reviews, vol. 19, 1996, pp. 401-424.

* cited by examiner

*Primary Examiner* — Kimberly A. Ballard
(74) *Attorney, Agent, or Firm* — Oblon, McClelland, Maier & Neustadt, L.L.P.

(57) ABSTRACT

Use of a variable fragment (VHH antibody) of a camelid single-chain antibody for the preparation of a peptide vector for delivering a substance of interest across the blood-brain barrier or into a cell.

27 Claims, 14 Drawing Sheets

SEQUENCE LISTING

```
<160> NUMBER OF SEQ ID NOS: 22

<210> SEQ ID NO 1
<211> LENGTH: 122
<212> TYPE: PRT
<213> ORGANISM: Camelidae

<400> SEQUENCE: 1

Ala Glu Val Gln Leu Gln Ala Ser Gly Gly Gly Ser Val Gln Pro Gly
1               5                   10                  15

Gly Ser Leu Arg Leu Ser Cys Ala Ala Ser Gly Phe Ile Phe Gly Trp
            20                  25                  30

Ser Thr Met Ser Trp Val Arg Gln Ala Pro Gly Lys Gly Leu Glu Trp
        35                  40                  45

Val Ser Thr Ile Ser Gly Gly Ser Ala Thr Thr Tyr Thr Asp Ser
    50                  55                  60

Val Lys Gly Arg Phe Thr Ile Ser Arg Asp Arg Ala Lys Asn Thr Leu
65                  70                  75                  80

Tyr Leu Gln Met Asn Ser Leu Lys Pro Glu Asp Thr Ala Ile Tyr Tyr
                85                  90                  95

Cys Asn Ala Asp Val Ser Thr Gly Phe Arg Tyr Gln Arg Lys Asp Tyr
            100                 105                 110

Trp Gly Arg Gly Thr Gln Val Thr Val Ser
        115                 120

<210> SEQ ID NO 2
<211> LENGTH: 114
<212> TYPE: PRT
<213> ORGANISM: Camelidae

<400> SEQUENCE: 2

Ala Glu Val Gln Leu Gln Ala Ser Gly Gly Gly Leu Val Gln Ala Gly
1               5                   10                  15
```

-continued

Gly Ser Leu Arg Leu Ser Cys Ala Ala Ser Gly Ser Thr Phe Arg Ile
            20                  25                  30

Asn Arg Met Gly Trp Tyr Arg Gln Ala Pro Gly Lys Gln Arg Glu Leu
            35                  40                  45

Val Ala Ser Ile Asn Ser Gly Gly Ser Thr Asn Tyr Ala Asp Ser Val
 50                  55                  60

Lys Gly Arg Phe Thr Ile Ser Arg Asp Asn Ala Lys Gly Thr Val Asn
 65                  70                  75                  80

Leu Thr Met Asn Ser Leu Lys Pro Glu Asp Thr Ala Val Tyr Tyr Cys
                     85                  90                  95

Asn Arg Val Thr Pro Trp Pro Tyr Trp Gly Gln Gly Thr Gln Val Thr
                100                 105                 110

Val Ser

<210> SEQ ID NO 3
<211> LENGTH: 118
<212> TYPE: PRT
<213> ORGANISM: Camelidae

<400> SEQUENCE: 3

Ala Glu Val Gln Leu Gln Ala Ser Gly Gly Gly Leu Val Gln Ala Gly
 1               5                  10                  15

Gly Ser Leu Arg Leu Ser Cys Ser Ala Ser Ala Ser Thr Thr Phe Ser
            20                  25                  30

Met Asn Thr Met Ala Trp His Arg Gln Ala Pro Gly Lys Gln Arg Ser
            35                  40                  45

Leu Val Ala Leu Ile Gly Ala Thr His Ser Ile Asn Tyr Glu Asp Ser
 50                  55                  60

Val Lys Gly Arg Phe Thr Ile Ser Arg Asp Asn Ala Lys Asn Thr Val
 65                  70                  75                  80

Tyr Leu Gln Met Ser Ser Leu Lys Pro Glu Asp Thr Ala Val Tyr Tyr
                     85                  90                  95

Cys Asn Asp Trp Tyr Trp Gln Met Lys Gly Gly Ser Trp Gly Gln Gly
                100                 105                 110

Thr Gln Val Thr Val Ser
        115

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
cgccatcaag gtaccagttg a                                             21

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5
gatgtgcagc tgcaggcgtc tggrggagg                                     29

<210> SEQ ID NO 6

```
<211> LENGTH: 45
<212> TYPE: DNA
<213> ORGANISM: Artificial Sequence
<220> FEATURE:
<223> OTHER INFORMATION: primer

<400> SEQUENCE: 6
catgccatga ctcgcggccc agccggccat ggccgakgts cagct            45

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
ggactagttg cggccgctga ggagacggtg acctg                       35

<210> SEQ ID NO 8
<211> LENGTH: 41
<212> TYPE: DNA
<213> ORGANISM: Artificial Sequence
<220> FEATURE:
<223> OTHER INFORMATION: primer

<400> SEQUENCE: 8
ggactagttg cggccgctgg ttgtggtttt ggtgtcttgg g                41

<210> SEQ ID NO 9
<211> LENGTH: 65
<212> TYPE: DNA
<213> ORGANISM: Artificial Sequence
<220> FEATURE:
<223> OTHER INFORMATION: primer

<400> SEQUENCE: 9
ggagatatat atccatgaga ggatcgcatc accatcacca tcacggatcc gccgakgtsc    60
agctg                                                        65

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
ccatataaag ctttgaggag acggtgacct g                           31

<210> SEQ ID NO 11
<211> LENGTH: 72
<212> TYPE: DNA
<213> ORGANISM: Artificial Sequence
<220> FEATURE:
<223> OTHER INFORMATION: primer

<400> SEQUENCE: 11
agaccacaac ggtttccctc tagaaataat tttgtttaac tttaagaagg agatatatcc    60
atgagaggat cg                                                72

<210> SEQ ID NO 12
<211> LENGTH: 49
<212> TYPE: DNA
<213> ORGANISM: Artificial Sequence
```

```
<220> FEATURE:
<223> OTHER INFORMATION: primer

<400> SEQUENCE: 12
atacgaaatt aatacgactc actataggga gaccacaacg gtttccctc          49

<210> SEQ ID NO 13
<211> LENGTH: 42
<212> TYPE: DNA
<213> ORGANISM: Artificial Sequence
<220> FEATURE:
<223> OTHER INFORMATION: primer

<400> SEQUENCE: 13
caggtcaccg tctcctcaaa gctttatatg gcctcggggg cc                 42

<210> SEQ ID NO 14
<211> LENGTH: 45
<212> TYPE: DNA
<213> ORGANISM: Artificial Sequence
<220> FEATURE:
<223> OTHER INFORMATION: primer

<400> SEQUENCE: 14
ccgcacacca gtaaggtgtg cggtttcagt tgccgctttc tttct              45

<210> SEQ ID NO 15
<211> LENGTH: 41
<212> TYPE: DNA
<213> ORGANISM: Artificial Sequence
<220> FEATURE:
<223> OTHER INFORMATION: primer

<400> SEQUENCE: 15
atacgaaatt aatacgactc actataggga gaccacaacg g                  41

<210> SEQ ID NO 16
<211> LENGTH: 126
<212> TYPE: PRT
<213> ORGANISM: Artificial Sequence
<220> FEATURE:
<223> OTHER INFORMATION: anti-GFAP VHH antibody fused to a His tag
<220> FEATURE:
<221> NAME/KEY: DOMAIN
<222> LOCATION: (1)..(118)
<223> OTHER INFORMATION: VHH antibody
<220> FEATURE:
<221> NAME/KEY: DOMAIN
<222> LOCATION: (119)..(126)
<223> OTHER INFORMATION: His tag

<400> SEQUENCE: 16

Asp Val Gln Leu Arg Ala Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
65                  70                  75                  80

Leu Gln Met Asn Ser Leu Lys Pro Glu Asp Thr Ala Val Tyr Tyr Cys
                85                  90                  95
```

```
Ala Ile Thr Gln Gln Gly Ser Gly Arg Gly Gln Glu Thr Gln Val Thr
            100                 105                 110

Val Ser Ser Ala Ala Ala Leu Glu His His His His His His
        115                 120                 125
```

<210> SEQ ID NO 17
<211> LENGTH: 126
<212> TYPE: PRT
<213> ORGANISM: Artificial Sequence
<220> FEATURE:
<223> OTHER INFORMATION: anti-GFAP VHH antibody fused to a His tag
<220> FEATURE:
<221> NAME/KEY: DOMAIN
<222> LOCATION: (1)..(118)
<223> OTHER INFORMATION: VHH antibody
<220> FEATURE:
<221> NAME/KEY: DOMAIN
<222> LOCATION: (119)..(126)
<223> OTHER INFORMATION: His tag

<400> SEQUENCE: 17

```
Asp Val Gln Leu Gln Val Ser Gly Gly Gly Ser Val Gln Pro Gly Gly
1               5                   10                  15

Ser Leu Arg Leu Ser Cys Ala Ala Pro Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Ala Ile Ser Arg Asp Asn Ala Lys Asn Thr Leu Ser
65                  70                  75                  80

Leu Gln Met Asn Ser Leu Lys Pro Glu Asp Thr Ala Ala Tyr Tyr Cys
                85                  90                  95

Ala Ile Thr Gln Gln Gly Ser Gly Arg Gly Arg Gly Thr Gln Val Thr
            100                 105                 110

Val Ser Ser Ala Ala Ala Leu Glu His His His His His His
        115                 120                 125
```

<210> SEQ ID NO 18
<211> LENGTH: 126
<212> TYPE: PRT
<213> ORGANISM: Artificial Sequence
<220> FEATURE:
<223> OTHER INFORMATION: anti-GFAP VHH antibody fused to a His tag
<220> FEATURE:
<221> NAME/KEY: DOMAIN
<222> LOCATION: (1)..(118)
<223> OTHER INFORMATION: VHH antibody
<220> FEATURE:
<221> NAME/KEY: DOMAIN
<222> LOCATION: (119)..(126)
<223> OTHER INFORMATION: His tag

<400> SEQUENCE: 18

```
Asp Val Gln Leu Gln Val Ser Gly Gly Gly Ser Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Tyr Trp Leu Arg Gln Ala Pro Gly Lys Gly Ile Glu Trp Val
        35                  40                  45

Ser Arg Ile Gly Pro Gly Gly Ser His Thr Glu Tyr Ala Asp Ser Val
    50                  55                  60

Lys Gly Arg Phe Thr Ile Ser Arg Asp Asn Ala Lys Asn Thr Leu Ser
```

```
                65                  70                  75                  80
Leu Gln Met Asn Ser Leu Lys Pro Glu Asp Thr Ala Val Tyr Tyr Cys
                    85                  90                  95

Ala Ile Thr Gln Gln Gly Ser Gly Arg Gly Gln Gly Thr Gln Val Thr
               100                 105                 110

Val Ser Ser Ala Ala Ala Leu Glu His His His His His His
               115                 120                 125

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
gggtctctga gactctcctc tgcagcctct gg                                   32

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
ccagaggctg cagaggagag tctcag                                          26

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
ctaccttgtt gcgtgatcgc agagtaatac acggccgt                             38

<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
acggccgtgt attactctgc gatcacgcaa caaggtagc                            39
```

VHH ANTIBODIES USED AS PEPTIDE VECTORS FOR DELIVERING A SUBSTANCE OF INTEREST

The present invention relates to the field of delivery of substances of interest across the mammal blood-brain barrier, in particular to a variable fragment of a camelid single-chain antibody capable of delivering a therapeutic or diagnostic compound across the mammal blood-brain barrier.

Drug delivery into the brain is often restricted by the blood-brain barrier (BBB), which regulates the exchange of substances between the peripheral circulation and the central nervous system (CNS). BBB acts first as an anatomical barrier because of the monolayer of endothelial cells, which are its main component. These cells exhibit specific properties such as the intercellular tight junctions, which prevent paracellular transport (Miller, 1999).

Antibodies represent potential neuro-diagnostic imaging agents for brain diseases as well as potential therapeutic agents such as immunoconjugates. However antibodies, like other large plasma proteins such as albumin, do not readily traverse cell membranes and are generally confined to the plasma compartment of the circulation.

One potential mechanism of enhanced delivery of antibodies molecules through the BBB is cationization, a process wherein cationization agent replaces surface carboxyl groups on the antibody with more basic groups, such as a primary amine group. The amount of cationization agent and reaction conditions are controlled so that the isoelectric point of the resulting cationized antibody is raised (Bickel et al., 2001). The positive charges of cationized proteins bind to negative charges on cellular surfaces and this interaction triggers absorptive-mediated endocytosis (AME) of the cationized protein into the cell. With respect to cationization of immunoglobulins, recent studies have shown that this method results in enhanced absorptive-mediated endocytosis by isolated brain capillaries in vitro (Girod et al., 1999) and at the cerebral microvasculature in vivo (Triguero et al., 1991), and that this endocytosis process leads to the net transcytosis of the cationized IgG into the brain in vivo.

A crucial point in the use of cationized antibodies is the retention of antigen binding properties. Cationized monoclonal antibodies show a decrease of affinity because arginine and lysine, usually involved in the binding with the antigen, are modified by the cationization process (Triguero et al., 1989). In addition, the possible antigenicity of cationized antibodies may represent another problem, since most monoclonal antibodies are mouse proteins, and in the case of administration to humans, cationization may enhance their pre-existing antigenicity.

A significant proportion of camelid antibodies are single-domain antibodies, which interact with their antigen via a single heavy-chain binding domain devoid of light chain. This domain is also referred to as "VHH" or "VHH antibody" or "VHH domain". Recombinant VHH antibodies present a minimal-sized and an intact antigen-binding domain. The absence of VL domain allows the VHH antibodies to attain a higher structural flexibility than that of VH domains associated with VL domains. Furthermore, the complementarity determining regions (CDRs) of VHHs, and especially CDR3, are statistically longer than those of conventional VH-VL antibodies (Muyldermans, 2001).

Receptor-mediated endocytosis (RME) of VHH antibodies have been proposed to represent an alternative to cationized antibodies. Abulrob et al. (2005) have described a positively charged variable fragment of a llama single domain anti-body (named FC5) that binds brain endothelial cells and transmigrates across the BBB in vitro and in vivo. The authors have excluded the endocytic pathway of FC5 by (1) macropinocytosis, since amiloride had no effect on transendothelial migration of FC5 and (2) absorptive-mediated endocytosis, since AME inhibitors failed to reduce trans-endothelial transport of FC5. The endocytic pathway of FC5 seems rather to be a receptor-mediated endocytosis since transcytosis of FC5 is dependant on clathrin-coated endocytotic vesicles and on the recognition of specific oligosaccharide anti-genic receptors on the luminal surface of human cerebral endothelial cells (HCEC).

Receptor-mediated endocytosis does however suffer from the major disadvantage that the quantity of a substance of interest delivered across the BBB is dependant on the presence and the number of a specific receptor expressed on the cerebral endothelial cells, as well as the number of non-saturated receptors.

Thus, there is a substantial interest in the development of adequate delivery systems to overcome the limitations of cationization AME (i.e., AME of cationized proteins) and RME.

International Application No. WO 2004/044204 describes variable fragments of camelid single-chain antibodies (VHH antibodies) capable of specifically binding the amyloid β peptide 42, a peptide involved in the pathogenesis of Alzeimer's disease (AD).

The Inventors have now found that unexpectedly certain of the VHH antibodies described in International Application No. WO 2004/044204 cross the BBB, by using an in vitro model. More specifically, the Inventors have shown that the VHH antibodies, having an isoelectric point above 8.5 (VHH V31-1 and VHH 61), were able to transmigrate across the BBB, by micropinocytosis and absorptive-mediated endocytosis (AME).

The Inventors have also prepared camelid single-chain antibodies directed against GFAP (glial fibrillary acidic protein) and have analysed their binding properties both in vitro and in vivo. Thus, one alpaca was immunized against hGFAP and three anti-GFAP VHH antibodies were selected by ribosome display.

The Inventors have unexpectedly demonstrated the ability of an anti-GFAP VHH antibody having an isoelectric point above 8.5, to diffuse, reach and bind its intracellular target in the brain after carotidian injection in vivo (as revealed by immuno-staining of astrocytes).

Thus, VHH antibodies directed against an intracellular target in a cell, such as a brain cell, and having an isoelectric point above 8.5, can be easily delivered to a tissue, such as brain, and penetrate into the cells, such as the neural and glial cells. Consequently, these VHH antibodies are interesting agents for imaging tissues or cells and delivering therapeutic compounds into the tissues or cells, particularly into the brain cells, such as the astrocytes.

Therefore, in a first aspect, the present invention relates to the use of a variable fragment (hereinafter denoted indifferently "VHH antibody" or "VHH domain") of a camelid single-chain antibody having an isoelectric point of at least 8.5, for the preparation of a peptide vector for delivering a substance of interest across a mammal blood-brain barrier, preferably a human blood-brain barrier, the brain transendothelial migration of said VHH antibody being inhibited in the presence of amiloride in vitro.

Said VHH antibody, which has naturally an isoelectric point superior or equal to 8.5, does not have a modified affinity for its antigen as it is the case for cationized monoclonal antibodies, and preferably does not bind nor recognize cerebromicrovascular endothelial cells; indeed it transmigrates across the BBB by micropinocytosis and/or absorptive-mediated endocytosis (AME).

Camelid (camel, dromedary, llama, alpaca, . . . ) VHH antibodies are known in the art (See Nguyen et al., 2001; Muyldermans, 2001).

The VHH antibody of the present invention has an isoelectric point of at least 8.5, preferably at least 9, more preferably at least 9.5, and furthermore preferably between 9.6 and 9.9.

Methods for determining the brain transendothelial migration of a VHH antibody in the presence of amiloride, a compound that inhibits the formation of macropinosomes without affecting coated pits-mediated endocytosis, are known in the art. One can refer to Weksler et al. (2005) and Abulrob et al. (2005). By way of example, an in vitro blood-brain barrier (BBB) model can be established by culturing an immortalizing human brain endothelial cell line, hCMEC/D3 (Weksler et al., 2005), on a porous filter. This cell line is available at the Collection Nationale de Cultures de Microorganismes (CNCM), 28 rue du Dr Roux, 75724 Paris Cedex 15, France, under the number 1-3308. This cell line retains most of the morphological and functional characteristics of brain endothelial cells, even without culture of glial cells and may thus constitute a reliable in vitro model of the human BBB. VHH antibody transendothelial migration is then tested in the presence of amiloride. The amiloride salt, preferably chlorhydrate (herein denoted "amiloride") concentration is preferably between 300 and 700 µM, more preferably about 500 µM.

The term "isoelectric point" (pI) refers to the pH at which the VHH antibody carries no net charge. Methods for determining the isoelectric point of a protein, particularly a peptide or protein, are well known to those of one skilled in the art. By way of example, many suitable computer programs for calculating the pI of a protein are generally known in the art, such as EMBOSS iep software, written by Alan Bleasby (ableasby@hgmp.mrc.as.uk), available at HGMP-RC, Genome Campus, Hinxton, Cambridge CB10 1SB, UK.

In a preferred embodiment, the VHH antibody of the invention consists of about 110 to 150 amino acid residues.

In a more preferred embodiment of the present invention, the VHH antibody comprises or consists of an amino acid sequence selected from the group consisting of SEQ ID NO: 1 (also denoted VHH V31-1) and SEQ ID NO: 2 (also denoted VHH 61-3). These VHHs have been described in International Application No. WO 2004/044204.

A host cell expressing VHH V31-1 is available at the Collection Nationale de Cultures de Microorganismes (CNCM), 28 rue du Dr Roux, 75724 Paris Cedex 15, France, under the number 1-2936; it was filed on Sep. 20, 2002.

A host cell expressing VHH 61-3 is also available at the CNCM, 28 rue du Dr Roux, 75724 Paris Cedex 15, France, under the number 1-2933; it was filed on Sep. 20, 2002.

Both VHH antibodies have the particularity to bind the amyloid β peptide 42 as described in International Application No. WO 2004/044204.

In another embodiment, said VHH antibody is directed against an intracellular target and said peptide vector is able to deliver a substance of interest into a mammal cell comprising said intracellular target.

In another embodiment of the present invention, the substance of interest according to the present invention may or may not permeate the mammal or human blood-brain barrier. If the substance of interest permeates said blood-brain, then the use of the VHH antibody of the present invention can allow enhancing the delivery of said substance of interest across the blood-brain barrier.

In an embodiment of the present invention, the substance of interest is a therapeutic or a diagnostic compound. Preferably, the size of the therapeutic or diagnostic compound is at least 400 Daltons and/or said compound has more than 8 hydrogen bonds.

In another embodiment of the present invention, the substance of interest is a liposome or a polymeric entity comprising a therapeutic or a diagnostic compound.

In a further embodiment of the present invention, the therapeutic or diagnostic compound is selected from the group consisting of a peptide, an enzyme, a nucleic acid, a virus, a fluorophore, a heavy metal, a chemical entity and a radioisotope.

Preferably, the diagnostic compound is selected from the group consisting of:
  enzymes such as horseradish peroxidase, alkaline phosphatase, glucose-6-phosphatase or beta-galactosidase;
  fluorophores such as green fluorescent protein (GFP), blue fluorescent dyes excited at wavelengths in the ultraviolet (UV) part of the spectrum (e.g. AMCA (7-amino-4-methylcoumarin-3-acetic acid); Alexa Fluor 350), green fluorescent dyes excited by blue light (e.g. FITC, Cy2, Alexa Fluor 488), red fluorescent dyes excited by green light (e.g. rhodamines, Texas Red, Cy3, Alexa Fluor dyes 546, 564 and 594), or dyes excited with far-red light (e.g. Cy5) to be visualized with electronic detectors (CCD cameras, photomultipliers);
  heavy metal chelates such as europium, lanthanum or yttrium;
  radioisotopes such as [$^{18}$F]fluorodeoxyglucose, $^{11}$C-, $^{125}$I-, $^{131}$I-, $^{3}$H-, $^{14}$C-, $^{35}$S, or $^{99}$Tc-labelled compounds.

In another embodiment of the present invention, the therapeutic compound is selected from the group consisting of an anticancer compound, an analgesic compound, an anti-inflammatory compound, an antidepressant compound, an anticonvulsant compound or an anti-neurodegenerative compound.

In another embodiment of the present invention, the VHH antibody as defined above is linked, directly or indirectly, covalently or non-covalently to the substance of interest as defined above.

Said substance of interest can be directly and covalently linked to said VHH antibody either to one of the terminal ends (N or C terminus) of the VHH antibody, or to the side chain of one of the amino acids of the VHH antibody. The substance of interest can also be indirectly and covalently linked to said VHH antibody by a connecting arm (i.e., a cross-linking reagent) either to one of the terminal ends of the VHH antibody or to a side chain of one of the amino acids of the VHH antibody. Linking methods of a substance of interest to an oligopeptide, in particular a VHH antibody, are known in the art (e.g., See Ternynck and Avrameas, 1987, "Techniques immunoenzymatiques" Ed. INSERM, Paris).

Many chemical cross-linking methods are also known in the art. Cross-linking reagents may be homobifunctional (i.e., having two functional groups that undergo the same reaction) or heterobifunctional (i.e., having two different functional groups). Numerous cross-linking reagents are commercially available. Detailed instructions for their use are readily available from the commercial suppliers. A general reference on oligopeptide cross-linking and conjugate preparation is: Wong, Chemistry of protein conjugation and cross-linking, CRC Press (1991).

Alternatively, if the substance of interest is a peptide, the VHH antibody of the invention and said substance of interest can be produced by genetic engineering as a fusion polypeptide that includes the VHH antibody and the suitable peptide. This fusion polypeptide can conveniently be expressed in known suitable host cells.

In a second aspect, the present invention provides a therapeutic or diagnostic agent comprising a VHH antibody as defined above, linked, directly or indirectly, covalently or non-covalently to a substance of interest as defined hereabove.

In a particular embodiment of the present invention, the therapeutic or diagnostic agent can be administered to a subject (a mammal or a human) by injection, preferably by intravenous, intraperitoneal, intramuscular or subcutaneous injection.

A diagnostic agent of the present invention can be used in brain imaging or in diagnosing brain disorders such as brain cancers (e.g., a glioma or a glioblastoma), pain, mental disorders or neurodegenerative disorders (e.g., Alzheimer's disease, Parkinson disease).

In another aspect, the present invention provides a kit for diagnosing a brain disorder as defined above, comprising at least a VHH antibody and a diagnostic compound as defined above.

In yet another aspect, the present invention provides a pharmaceutical composition comprising a therapeutic agent as defined above and a pharmaceutically acceptable carrier.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

In yet another aspect, the present invention provides a therapeutic agent or a pharmaceutical composition as defined above for use in the treatment of brain cancers, pain, mental disorders or neurodegenerative disorders.

The term "treatment" includes the administration of the therapeutic agent or a pharmaceutical composition as defined above to a patient who has a disorder, a symptom of disorder or a predisposition toward a disorder, with the purpose to cure, heal, alleviate, relieve, alter, remedy, ameliorate, improve or affect the disorder, the symptoms of the disorder, or the predisposition toward disorder.

In yet another aspect, the present invention relates to the use of a variable domain of a camelid heavy-chain antibody (VHH antibody) directed against an intracellular target and having an isoelectric point of at least 8.5, preferably of at least 9, and more preferably between 9 and 10, or of a polypeptide or antibody comprising said VHH antibody, for targeting said intracellular target or for the preparation of a peptide vector for delivering a substance of interest, as defined above, into a mammal cell, preferably a human cell, comprising said intracellular target.

As used herein the term "intracellular target" refers to any antigen (or moiety) present inside a cell, preferably a brain cell, such as a neuron or a glial cell, and capable of directing a VHH antibody, polypeptide or antibody, as defined above, inside said cell by virtue of its ability to bind or interact with said VHH antibody.

As used herein the term "targeting" refers to the ability of a VHH antibody, polypeptide or antibody, as defined above, to enter a cell, preferably a brain cell, such as a neuron or a glial cell, and bind said intracellular target (antigen).

In a preferred embodiment of this aspect, said VHH antibody is hyperstable.

As used herein, the term "hyperstable" means that a VHH antibody can recover its active activity (or function) after denaturation by heat (then said VHH antibody is thermostable) and/or after reduction of its disulfide bridge(s).

The thermostability of a VHH antibody can be determined as follows:
a) suspending a VHH antibody (named "native VHH antibody") in PBS/NaCl 300 mM,
b) heating for 15 minutes at 75° C.,
c) cooling down at 4° C. for 20 minutes,
d) determining the binding affinity of the refolded VHH antibody obtained at step c), and if the stability of the refolded VHH antibody is reduced at most twice compared to the native VHH antibody then said VHH antibody is thermostable.

The reduction of the disulfide bridge(s) of a VHH antibody can be carried out as described in Example 3. According to the present invention, a VHH antibody is hyperstable if the binding affinity of a VHH antibody, of which the disulfide forming cysteine residues have been replaced with serine residues, is reduced at most twice compared to the native VHH antibody.

The binding affinity of a VHH antibody can be determined by any method known from one skilled in the art, for instance by the ELISA technique described in Example 2 below.

In another preferred embodiment of this aspect, said human cell is an astrocyte, and optionally said intracellular target is a GFAP.

In addition to the preceding features, the invention further comprises other features which will emerge from the following description, which refers to examples illustrating the present invention, as well as to the appended figures.

FIG. 1 shows VHH antibody transmigration across in vitro blood-brain barrier (BBB) model. Transport studies were initiated by adding 10-20 µg/ml VHH antibodies (V31-1, 61-3 and L1-3) to apical compartment (upper chamber) and the amount of VHH antibodies was determined in the lower chamber at 10 min, 30 min and 60 min.

FIG. 2 shows the effects of pharmacological inhibitors of adsorptive-mediated endocytosis (AME) and macropinocytosis on transmigration of VHH antibodies across in vitro BBB model. hCMEC/D3 were pretreated for 30 min with AME inhibitors, protamine sulfate (40 µg/ml), and poly-L-lysine (300 µM), or micropinocytosis inhibitor, amiloride (500 µM), and VHH antibodies (V31-1 and 61-3) transport was measured over 30 min.

FIG. 3 shows the energy-dependence of VHH antibody transmigration across in vitro BBB barrier model. Transcellular migration of VHH antibodies (V31-1 and 61-3) across hCMEC/D3 was measured at 37° C. and 4° C. VHH antibodies transmigration was measured at 30 min after addition to upper chamber.

Figure 6:
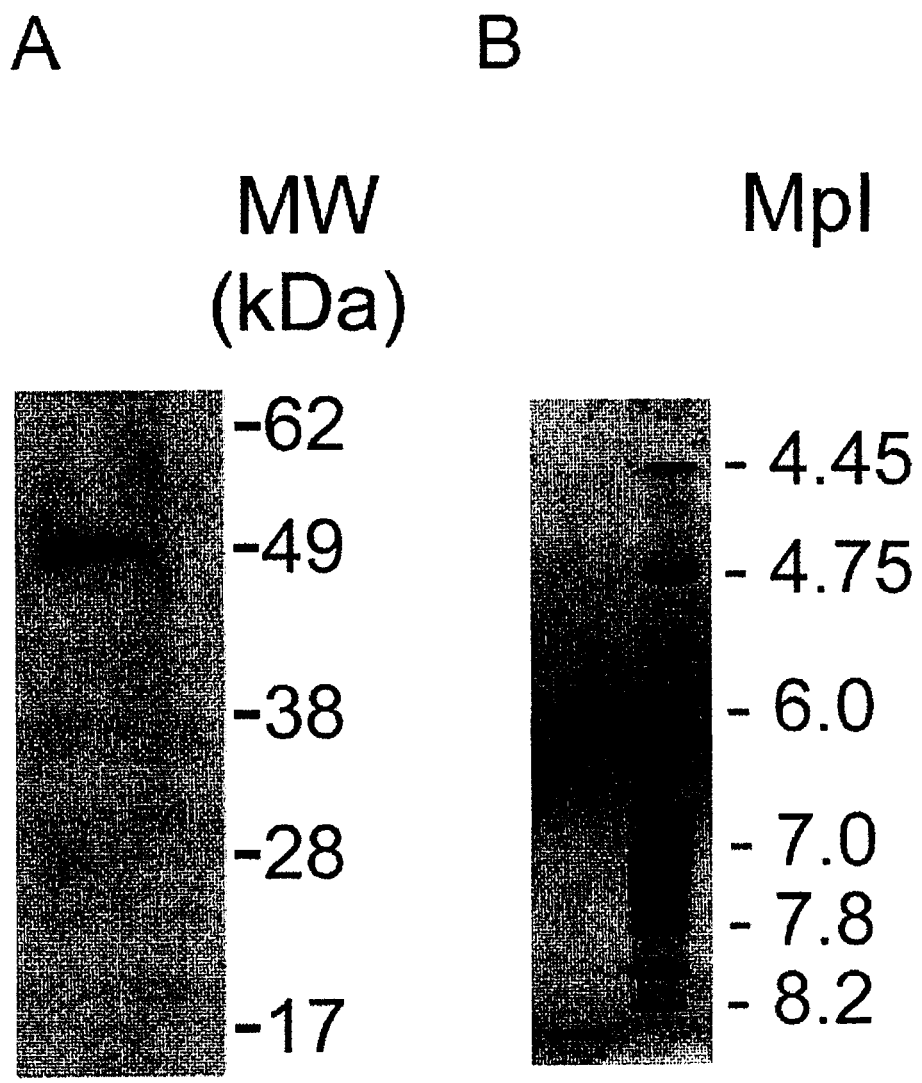

FIG. 6 shows the characterization of anti-GFAP VHH-E9. A: Western blot. Murine brain extracts were electrophoresed, immunoblotted and incubated with VHH-E9. MW: molecular weight marker proteins. B: Isoelectric focusing on PhastGel IEF 3-9. MpI: isoelectric point marker.

Figure 7:
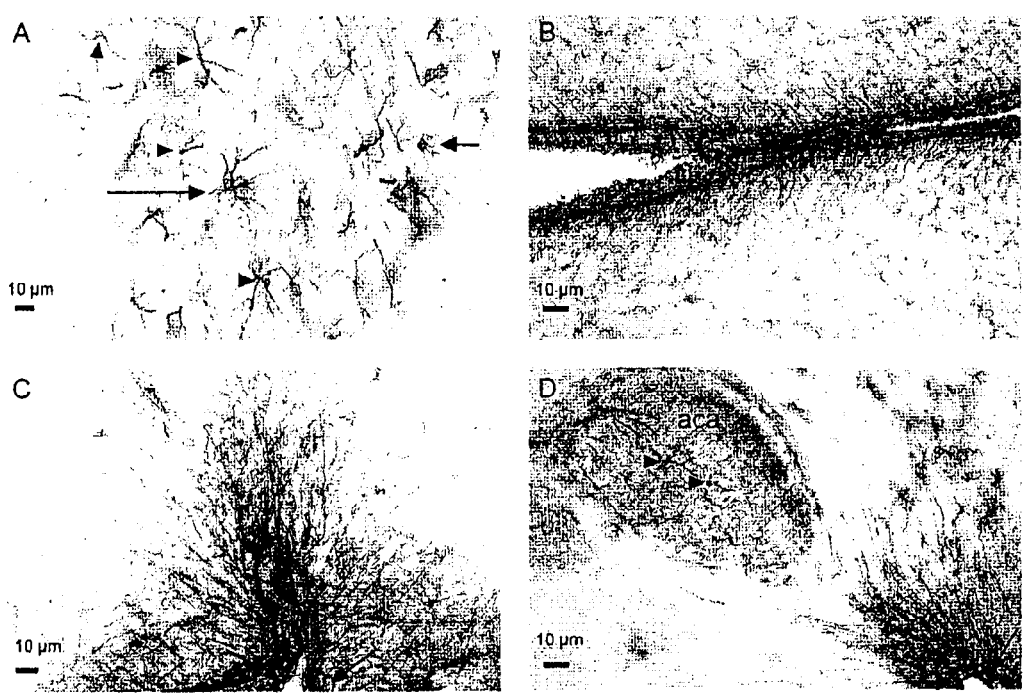

FIG. 7 shows the VHH-E9 immunolabeling of GFAP in the cytoplasm of astrocytes in mouse brain sections. A: Immunolabeled astrocytes in the white matter between striatum and primary motor cortex, close to the corpus callosum. It was mainly identify thin fibrous astrocytes (arrowheads) and some large protoplasmic astrocytes (arrow). B: immunolabeled astrocytic radially oriented processes beaming from the pial surface glia limitans (arrows) at level of the dorsal third ventricle. C: immunolabeled astrocytic radially organized glial processes beaming from the pial surface glia limitans (arrows) located at the base of the forebrain. These processes spread out through the antero-ventral periventricular and medial preoptic nuclei. D: immunolabeled astrocytes processes located in the cylindrical white matter of the anterior commissure, anterior part (aca; arrowheads). In the vicinity of aca are located also radially oriented immunolabeled GFAP fibers. These glial processes are beaming from a folded portion of the pial surface located in the bottom of the lateral ventricle (arrows).

Figure 8:
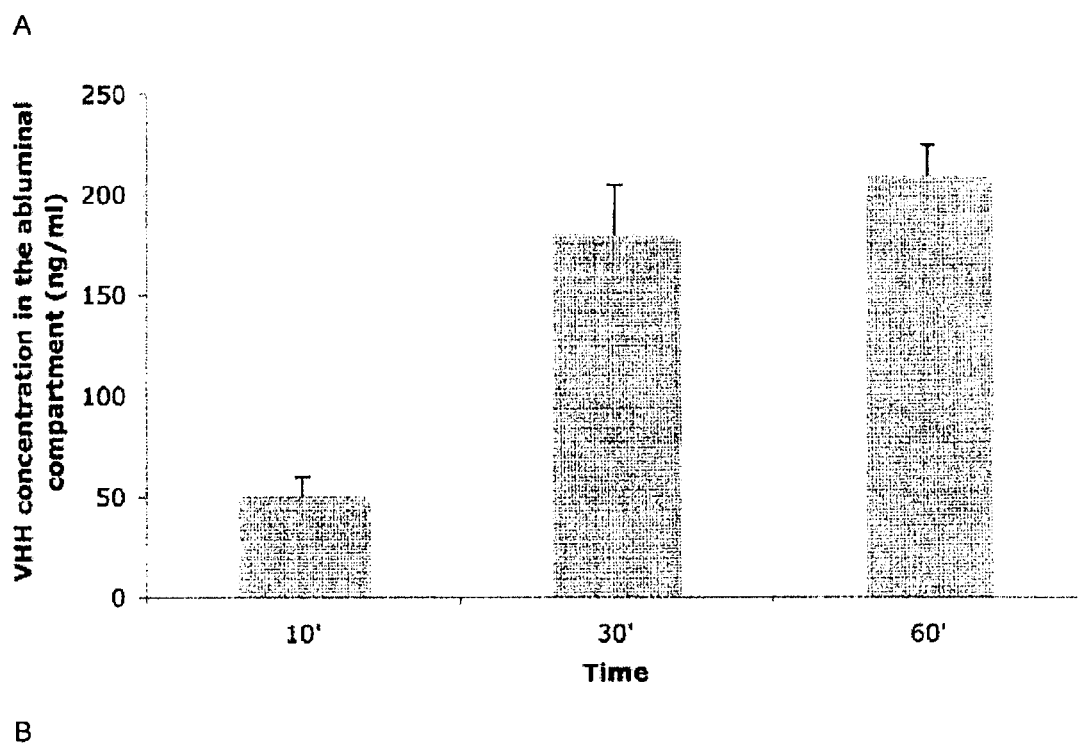
Figure 8:
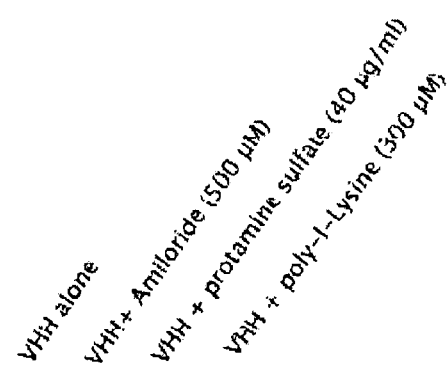

FIG. 8 shows the VHH-E9 transmigration across in vitro blood-brain barrier (BBB). A: Transport studies were initiated by adding 10-20 µg/ml VHH to the apical compartment (upper chamber) and the amount of VHH was determined in the lower chamber after 10 min, 30 min and 60 min. B: Effects of pharmacological inhibitors of adsorptive-mediated endocytosis (AME) and macropinocytosis on transmigration of VHH across in vitro BBB model. hCMEC/D3 were pre-treated for 30 min with either AME inhibitors, protamine sulfate (40 µg/ml), and poly-L-lysine (300 µM), or micropinocytosis inhibitor, amiloride (500 µM). VHH transport was then measured over 30 min.

Figure 9:
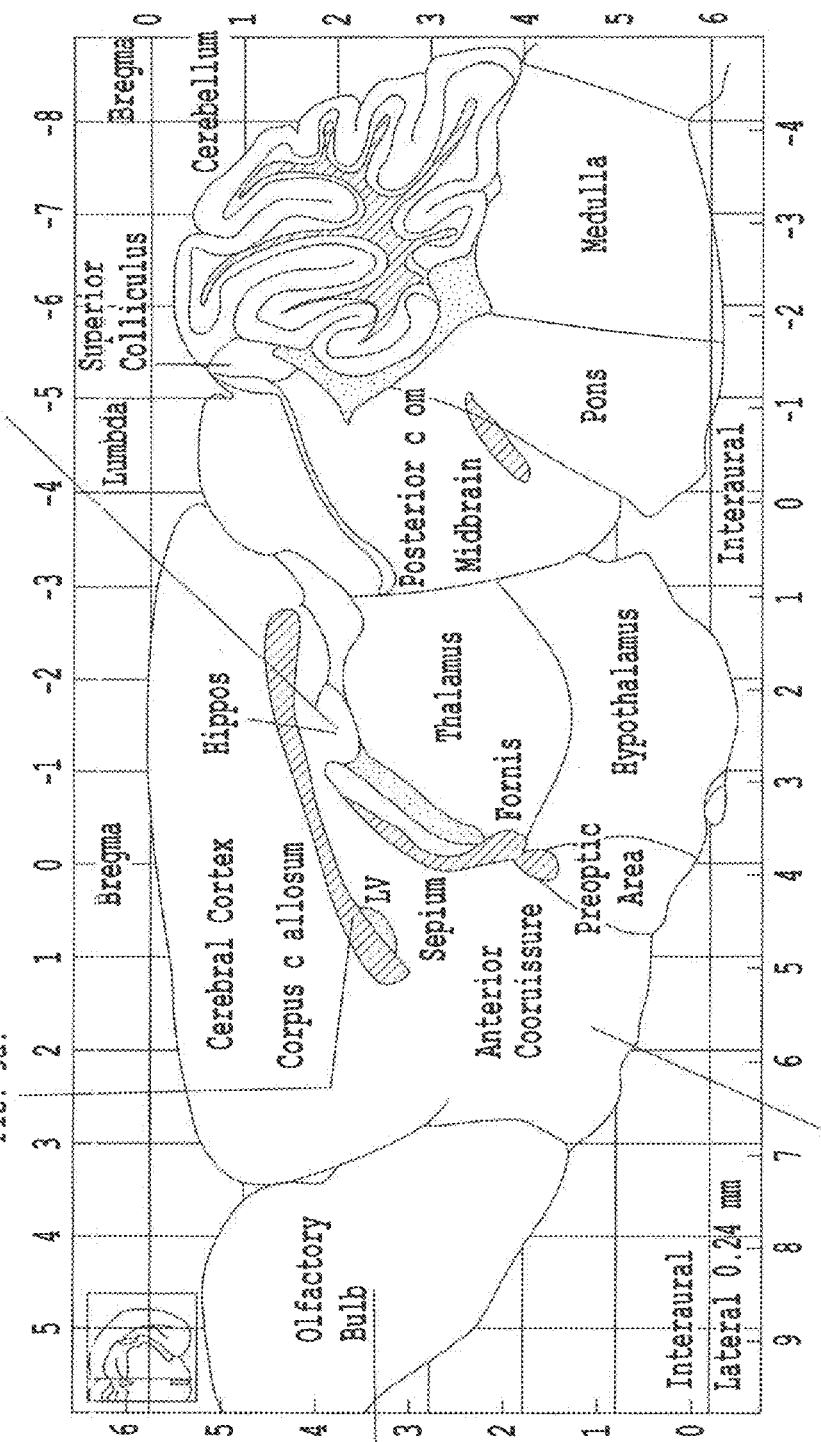
Figure 9A:
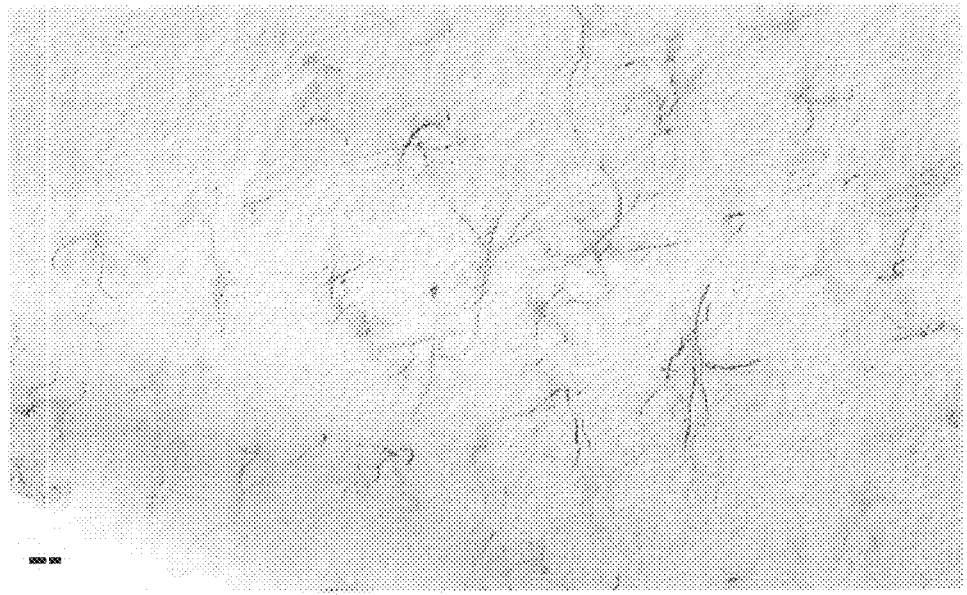

FIG. 9 shows the VHH-E9 transmigration across blood-brain barrier (BBB) in vivo. 4 mg of VHH were perfused in the left carotide artery of C57BL/6 mice for 60 min. Mice were euthanized 1 hour later. Immunolabeled astrocytes in, a: the corpus callosum, b: hippocampus, c: olfactory bulb, d: gray matter (scale bar: 10 µm), e: coronal section of the rostral corpus callosum. More astrocytes are labelled in left (L) genu of the corpus callosum (arrow), ipsilateral to the injected carotide artery, as compared to the right side (R) (scale bar: 100 µm).

Figure 10:
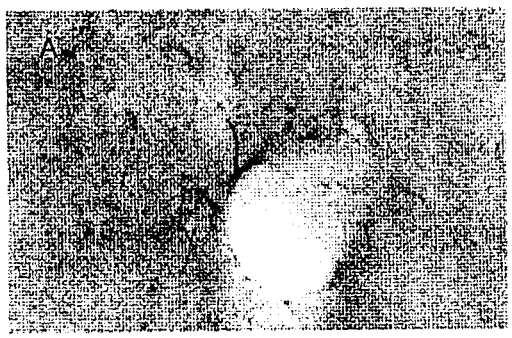
Figure 10:
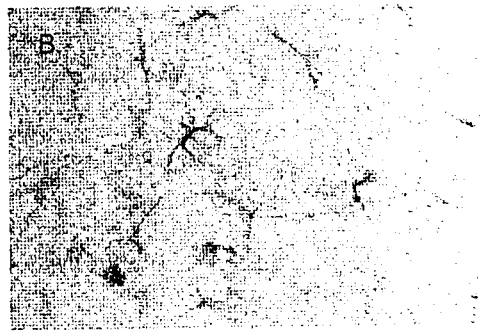

FIG. 10 shows the VHH-E9 immunolabelling of GFAP in mouse brain sections after injection of 30% mannitol. a: Glial astrocytic foot process apposed to a blood vessel, b: VHH immunolabelling of astrocytes in the white matter.

Figure 11:
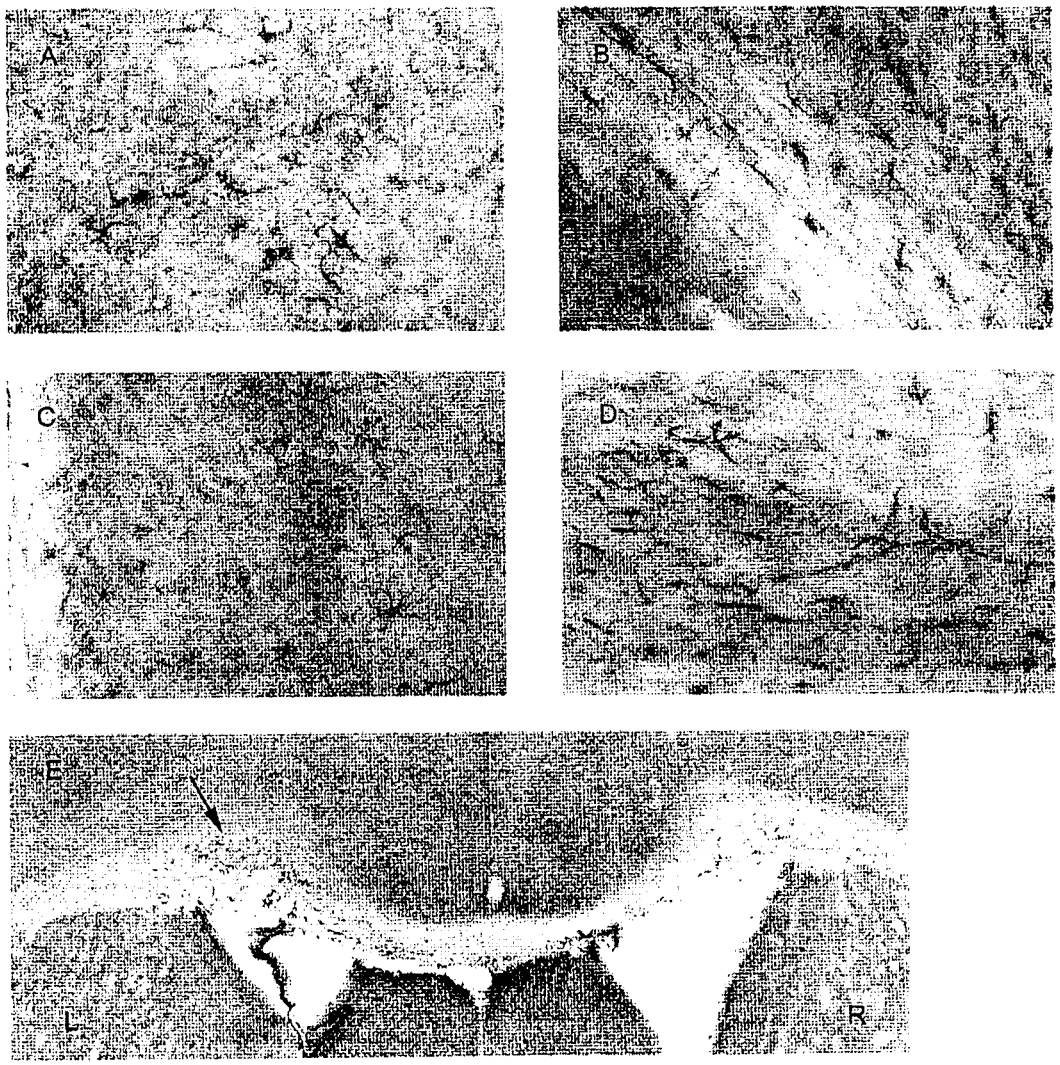

FIG. 11 shows the VHH-E9 labelling of GFAP in the cytoplasm of mice brain sections after infection with Pl. berghei parasite. C57BL/6 mice were inoculated i.p. with $10^6$ infected erythrocytes of Pl. berghei per mouse. At day 5, 400 µg of VHH were perfused in the left carotide for 60 min. Mice were killed 1 hour later. A: olfactif bulb, B: White matter, C: hippocampus, D: Caudal region, E: coronal section of the white matter. Astrocytes are labelled in the corpus callosum (L is the left hemisphere, corresponding to the side of the injected carotid; R is the right hemisphere).

EXAMPLE 1

In Vitro VHH Antibody Transmigration Across HCMEC/D3 Materials and Methods

1) Materials and Methods
Materials
EBM-2 medium was from Clonetics (Cambrex Bio-Science, Wokingham, UK) and was supplemented with VEGF, IGF-1, EGF, basic FGF, hydrocortisone, ascorbate, gentamycin and 2.5% fetal bovine serum (FBS) as recommended by the manufacturer: this fully supplemented medium is designated Microvascular Endothelial Cell Medium-2 (EGM-2 MV, herein referred to as EGM-2 medium). Collagen type I was obtained from BD Biosciences PharMingen (Le Pont de Claix, France).

VHH Antibodies and Expression Thereof in a pET System
VHH V31-1 (SEQ ID NO: 1)
VHH 61-3 (SEQ ID NO: 2)
VHH L1-3 (SEQ ID NO: 3)
The coding sequences of VHH V31-1, VHH 61-3 and VHH L1-3 antibodies in vector pHEN1, described in International Application No. WO 2004/044204, were subcloned in vector pET 22 using the NcoI and NotI restriction sites according to the manufacturer's instructions (Novagen, Darmstadt, Germany). Transformed E. coli BL 21 (DE3) cells expressed VHH antibodies in the periplasm after induction by IPTG 1 mM for 3 hours at 20° C. Periplasmic extracts were obtained by spheroplasting cells, suspended in 50 mM sodium phosphate buffer pH 8 containing 20% sucrose and 1 mM EDTA, and hydrolysing the peptidoglycan with 5 mg/ml lysozyme for 20 min at 4° C., in the presence of protease inhibitors (Complete™, Boehringer Mannheim, Germany). The suspension was then centrifuged 2 min at 10,000 rpm. The supernatant corresponding to the periplasmic extract was kept at 4° C. Purified VHH antibodies were obtained by IMAC using a chelating agarose column charged with $Ni^{2+}$ (Superflow Ni-NTA, Qiagen Ltd, UK) according to manufacturer's instructions. The protein content was measured using the Bradford reagent. The purity of the final preparation was evaluated by SDS-PAGE with Coomassie staining and by Western blot.

The amino acid sequences of SEQ ID NO: 1, 2 and 3 have been described in International Application No. WO 2004/044204.

The pI calculation of these VHH antibodies has been performed using EMBOSS iep software. VHH V31-1 and VHH 61-3, have a basic pI, respectively 9.69 and 9.83, while VHH L1-3 has a pI of 7.67.

Transport Across an In Vitro Blood Brain Barrier
Immortalized human brain endothelial cells hCMEC/D3 have been previously described in detail in Weksler et al. (2005). Cell viability in the presence of VHH antibodies was assessed by MTT assay as described in Hussain et al., 1993.

The permeability of hCMEC/D3 cell monolayers to VHH antibodies was measured on transwell polycarbonate insert filters (pore size 3 µm, Corning, Brumath, France) as described in Weksler et al. (2005). hCMEC/D3 cells were seeded on the filters at a confluent density of $2 \times 10^5$ cells/$cm^2$ in EGM-2 medium.

Transport studies were performed 3 days post-seeding as described in Weksler et al. (2005). Experiments were initiated by adding VHH antibodies to the upper chamber containing either collagen, coated inserts without cells, hCMEC/D3 cells or hCMEC/D3 cells pre-exposed to various pharmacological modulators for 30 min. Transport studies were conducted at 37° C. The lower chamber was sampled at various time intervals (10, 30 and 60 min) and the presence of VHH antibodies was determined by ELISA and Western Blot (see below).

ELISA
A modified version of a standard ELISA was used to test for the presence of VHH antibodies in culture supernatants. Microtiter plates (Nunc, Denmark) were coated by incubation overnight at 4° C. with 1 µg/ml of antigen diluted in PBS. Plates were washed four times with buffer A (0.1% Tween 20 in PBS), and VHH antibodies were diluted in buffer B (0.5% gelatin in buffer A). The plates were incubated for 2 hours at 37° C. and washed again, before adding a rabbit anti-His tag antibody (Santa Cruz, Calif., USA), then the plates were washed with buffer A and a goat anti-rabbit IgG antibody labeled to peroxidase (ICN, aurora, OH) or labeled to β-galactosidase (Biosys, les Ullis, France) was added for 1 hour at 37° C.

Western Blot

For immunoblot detection of VHH antibodies, a modified version of a standard western blot was used. To an aliquot, an equal volume of gel loading buffer was added and then treated at 100° C. for 5 min. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution and revealed by peroxidase-labeled rabbit anti-His tag (Santa Cruz, Calif., USA) followed by peroxidase labeled goat anti-rabbit immunoglobulins. Finally, peroxidase activity was visualized using a chemiluminescent kit (Amersham).

2) Results

Figure 1:
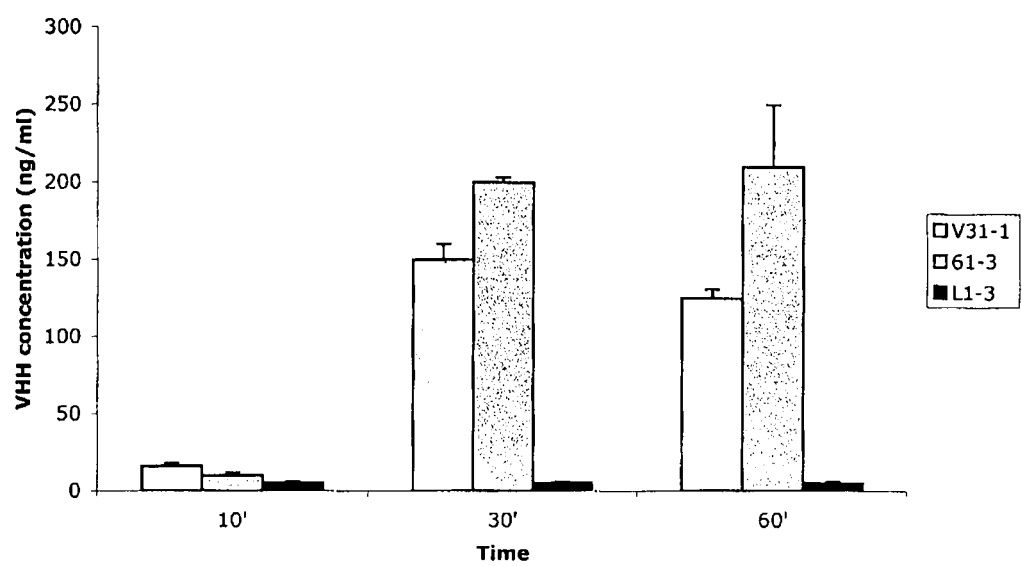

Transcytosis assay were performed on an in vitro BBB model described in Weksler et al. (2005). VHH antibodies were added to the upper chamber and the rate of passage of VHH antibodies from the luminal to the abluminal side of the cell monolayer was measured. FIG. 1 shows that there is a transcytosis of functional VHH V31-1 and VHH 61-3 while there is no passage of VHH L1-3 across hCMEC/D3. This passage was time-dependant and reached a maximum at 30 min. At 60 min about 1% of VHH antibodies were present in the lower chamber.

Figure 2:
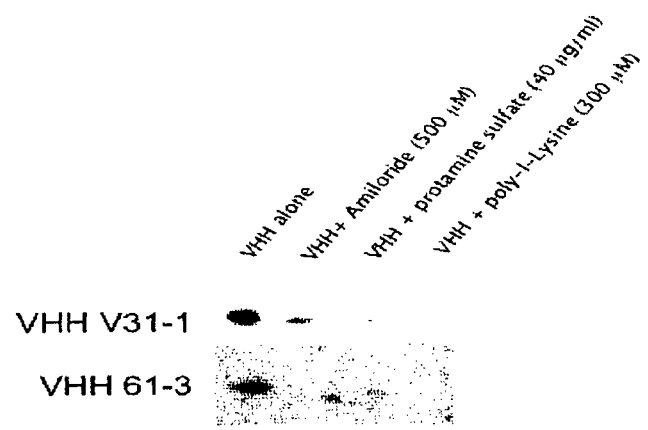

The contribution of adsorptive-mediated endocytosis (AME) to VHH antibody transcytosis was assessed. HCMEC/D3 were preincubated for 30 min with highly cationic protamine sulfate (40 µg/ml) or a commercially available polylysine (300 µM); both previously shown to inhibit AME prior to assessing VHH antibody uptake and transport (Abulrob et al., 2005). There was an inhibition of the transendothelial migration of VHH antibodies suggesting that the transmigration is charge-dependant (FIG. 2).

To investigate whether VHH V31-1 and VHH 61-3 antibodies are internalized and transported by macropinocytosis, VHH antibody transmigration was tested in the presence of 500 µM amiloride chlorhydrate, a compound that inhibits the formation of macropinosomes without affecting coated pits-mediated endocytosis. Amiloride had an inhibitory effect on transendothelial migration of these VHH antibodies (FIG. 2).

Figure 3:
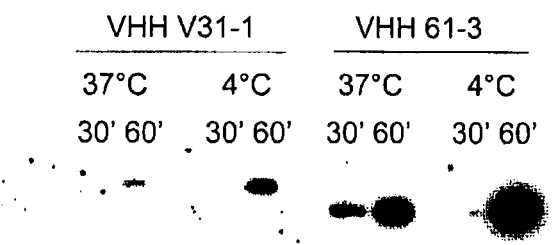
Figure 4:
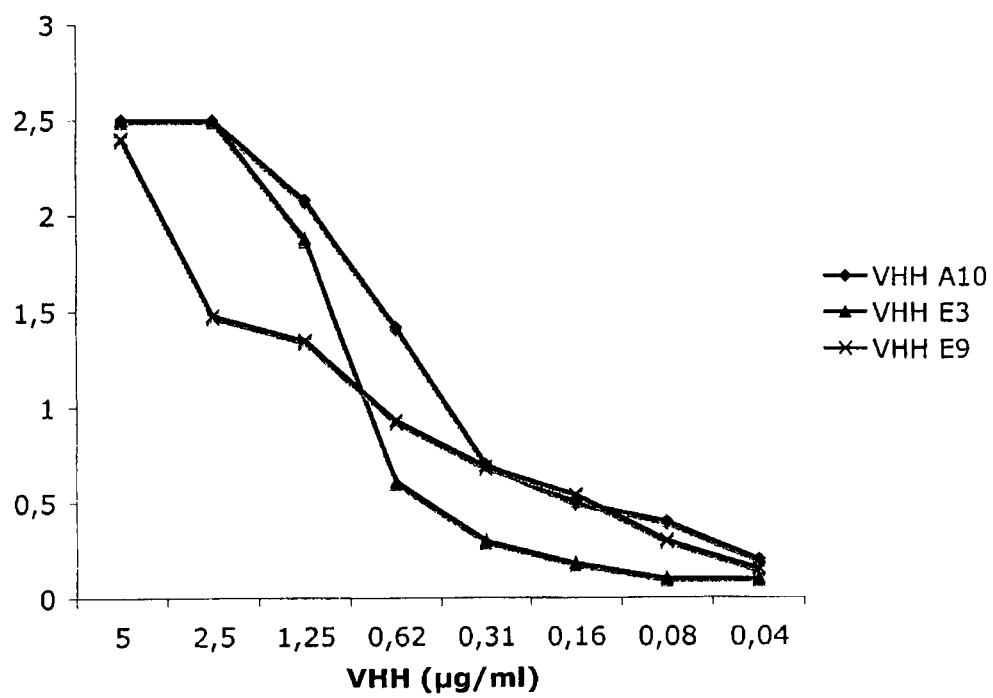
FIG. 4 shows the binding of the VHH domains VHH-A10, -E3 and -E9 to GFAP analysed by ELISA. Microtiter plates were coated with GFAP and various concentrations of VHH were added.

To investigate the energy dependence of VHH V31-1 and VHH 61-3 antibody transcytosis, transport was measured at 37° C. and at 4° C. At 30 min, marked reductions of transendothelial migration of these VHH antibodies was observed at 4° C. compared with 37° C. suggesting that their transport across hCMEC/D3 is energy dependent (FIG. 3).

EXAMPLE 2

Production of Anti-GFAP-VHHs

1) Materials and Methods

Materials

GFAP (gi:164694994 in the GENBANK database) from normal human brain was purchased from United States Biological, Inc. The anti-GFAP rabbit polyclonal antibody (GF 5) was obtained from Santa Cruz Biotechnology, Ca, USA.

Primers:

```
CH2FORTA4 (SEQ ID NO: 4):
5'-CGCCATCAAGGTACCAGTTGA-3'

VHBACKA6 (SEQ ID NO: 5):
5'-GATGTGCAGCTGCAGGCGTCTGGRGGAGG-3'

VHBACKA4 (SEQ ID NO: 6):
5'-CATGCCATGACTCGCGGCCCAGCCGGCCATGGCCGAKGTSCAGC
T-3'

VHFOR36 (SEQ ID NO: 7):
5'-GGACTAGTTGCGGCCGCTGAGGAGACGGTGACCTG-3'

LH (SEQ ID NO: 8):
5'-GGACTAGTTGCGGCCGCTGGTTGTGGTTTTGGTGTCTTGGG-3'

VHH-SPEF (SEQ ID NO: 9):
5'GGAGATATATATCCATGAGAGGATCGCATCACCATCACCATCACGGAT
CCGCCGAKGTSCAGCTG-3'

VHH-SPER (SEQ ID NO: 10):
5'-CCATATAAAGCTTTGAGGAGACGGTGACCTG-3'

SDA-MRGS (SEQ ID NO: 11):
5'AGACCACAACGGTTTCCCTCTAGAAATAATTTTGTTTAACTTTAAGAA
GGAGATATATCCATGAGAGGATCG-3'

T7C primer (SEQ ID NO: 12):
5'ATACGAAATTAATACGACTCACTATAGGGAGACCACAACGGTTTCCCT
C-3'

VHH-link (SEQ ID NO: 13):
5'-CAGGTCACCGTCTCCTCAAAGCTTTATATGGCCTCGGGGGCC-3'

TolAkurz (SEQ ID NO: 14):
5'-CCGCACACCAGTAAGGTGTGCGGTTTCAGTTGCCGCTTTCTTTC
T-3'

T7B (SEQ ID NO: 15):
5'-ATACGAAATTAATACGACTCACTATAGGGAGACCACAACGG-3'
```

Antigen Preparation and Induction of a Humoral Immune Response in Alpaca

250 µl of GFAP (1 mg/ml) was mixed with 250 µl of Freund complete adjuvant for the first immunization, and with 250 µl of Freund incomplete adjuvant for the following immunizations.

One young adult male alpaca (*Lama pacos*) was immunized at days 0, 21 and 35 with 250 µg of the immunogen. The alpaca was bled and the immune response was monitored by titration of serum samples by ELISA on GFAP (1 µg/ml in PBS) immobilized on MaxiSorp™ plates (Nunc, Denmark), after dilution of the serum in PBS-Tween 0.1% containing 0.5% gelatin. The bound alpaca antibodies were detected with polyclonal rabbit anti-alpaca IgG (obtained by immunizing rabbits with alpaca immunoglobulins isolated with protein A and protein G columns [Muyldermans et al., 1994] and horseradish peroxidase-labeled goat anti-rabbit antibodies.

Library Construction

The blood of the immunized animal was collected and the peripheral blood lymphocytes were isolated by centrifugation on a Ficoll (Pharmacia) discontinuous gradient and stored at −80° C. until further use. Total RNA and cDNA was obtained as previously described by Lafaye et al., 1995. DNA fragments encoding VHH domains were amplified by PCR using CH2FORTA4 and VHBACKA6 primers (described in International Application No. WO 2004/044204; Lafaye et al., 1995), which respectively anneal to the 3' and 5' flanking region of VH genes (Arbabi Ghahroudi et al., 1997). The amplified product of approximately 600 bp was subjected to a second round of PCR using either the primers VHBACKA4 and VHFOR36 or the primers VHBACKA4 and LH specific of the long hinge antibody (as described in International Application No. WO 2004/044204). The primers were complementary to the 5' and 3' ends of the amplified product and incorporated SfiI and NotI restriction sites at the ends of the VHH genes. The PCR products were digested and ligated into phage vector pHEN 1 (Hoogenboom and Winter, 1992). The resulting library was composed of two sublibraries, one derived from VHH DNA-encoding genes with no hinge and the other from long hinge antibody genes.

The VHH domain population was converted to ribosome display format using PCR and transcribed to mRNA as follows (Mouratou et al., 2007). Clones from the VHH domain population were amplified using the primer VHH-SPEF that contained a 5' extension containing the prokaryotic Shine-Dalgarno sequence and the primer VHH-SPER. The 400 bp PCR product was then amplified using a mixture of SDA-MRGS primer (5 µM), VHH—SPER primer (5 µM) and T7C primer (5 µM). The 450 bp product was purified with the Wizard® SV purification kit (Promega).

A peptide linker was added to ensure that the protein displayed on the ribosome was accessible to potential ligands. DNA encoding this linker, corresponding to a part of the *E. coli* protein TolA was PCR amplified by using the primers VHH-link and TolAkurz.

Finally the library was assembled with the TolA linker by PCR assembly using primers TolAkurz and T7B.

The final assembly product corresponded to a library of VHH with all of the 5' and 3' regions necessary to its use for ribosome display selections, as previously described (Mouratou et al., 2007).

Ribosome Display Selection Rounds

GFAP (10 µg/ml) was bound in a MaxiSorp™ plate (Nunc, Denmark) and selections by ribosome display were performed at 4° C. Selection was performed according to Mouratou et al., 2007. The wells were blocked with 300 µl 0.5% BSA in TBS for 1 hour at room temperature. Before the ribosome-display round, the wells were then extensively washed with washing buffer WBT (50 mM Tris acetic acid, pH7.5, 150 mM NaCl, 50 mm Mg(CH3COO⁻)$_2$, 0.05% tween 20). A ribosome display round consisted of a 15 nm-prepanning step on a well coated with PBS and a 1 hour binding step on the target protein. After washing, RNA purification and reverse transcription (with primer VHH-SPER), a first PCR was done using the primers VHH-SPEF and VHH-SPER. This RT-PCR product was purified on an agarose gel and reamplified in a second PCR using T7C, SDA-MRGS and VHH-SPER primers. This PCR product was purified on an agarose gel and reamplified in a third PCR using T7B and TolAkurz primers. The third PCR product served as template for the next round of ribosome display. Three identical rounds of selection were performed to isolate high-affinity binders.

VHH Expression Either with a His-tag or with a CH2 Domain, Allowing its Recognition by Anti-Tag or Anti-Alpaca Antibodies VHH Expression with a his-Tag in the pET System The coding sequence of the VHH was subcloned in vector pET22 using the NcoI and NotI restriction sites according to the manufacturer's instructions (Novagen, Darmstadt, Germany). Transformed *E. coli* BL 21 (DE3) cells expressed VHHs in the periplasm after induction by IPTG 1 mM for 18 hours at 15° C. Periplasmic extracts were obtained by spheroplasting cells, suspended in 50 mM sodium phosphate buffer pH 8 containing 20% sucrose and 1 mM EDTA, and hydrolysing the peptidoglycan with 5 mg/ml lysozyme for 20 min at 4° C., in the presence of protease inhibitors (Complete™, Boehringer Mannheim, Germany). The suspension was then centrifuged 2 min at 10,000 rpm. The supernatant corresponding to the periplasmic extract was kept at 4° C. Purified VHHs were obtained by IMAC using a chelating agarose column charged with Ni$^{2+}$ (Superflow Ni-NTA, Qiagen Ltd, UK) according to manufacturer's instructions. Purified VHH were dialysed against PBS and the protein content was measured using the Bradford reagent. The purity of the final preparation was evaluated by SDS-PAGE with Coomassie staining and by Western blot.

Expression of VHH with the CH2 Domain

Anti-His tag antibodies may prove to be difficult to use in immunohistochemistry experiments. This is why VHHs coupled with the CH2 domain were also prepared. Specific and sensitive rabbit anti-alpaca antibodies directed against the CH2 domain are available (LAFAYE et al., 2009). Secondary anti-rabbit antibodies conjugated with horseradish peroxidase are routinely used in Neuropathology laboratories. The alpaca Immunoglobulin CH2 domain was amplified by RT-PCR using primer CH2-Fwd-Not and CH2-Rev-Xho (Lafaye et al., 2009). These primers contain respectively a NotI and a XhoI site allowing the cloning of CH2 domain in pET 22 vector in frame with VHH gene. The expression and purification of VHH were performed as described in Lafaye et al., 2009.

Enzyme-Linked ImmunoSorbent Assay (ELISA)

A modified version of a standard ELISA was used to test for the presence of VHH in culture supernatants. Microtiter plates (Nunc, Denmark) were coated by incubation overnight at 4° C. with 5 µg/ml of antigen diluted in PBS. Plates were washed four times with buffer A (0.1% Tween 20 in PBS), and VHHs were diluted in buffer B (0.5% gelatin in buffer A). The plates were incubated for 2 hours at 37° C. and washed again, before adding a horseradish peroxidase-labeled rabbit anti-c-myc (A14) (Santa Cruz Biotechnology, Ca, USA) or with a rabbit anti-His tag antibody (Santa Cruz, Ca, USA). Then, the plates were washed with buffer A, and freshly prepared 0.2% orthophenylenediamine (Dakopatts A/S, Glostrup, Denmark), 0.03% H$_2$O$_2$ in 0.1 M citrate buffer, pH 5.2, were added to each well. The peroxidase reaction was stopped by adding 3 M HCl, and the optical density was measured at 490 nm.

Determination of Dissociation Constants by ELISA

The binding affinity of VHHs was determined as described by Friguet et al., 1985. Briefly, various concentrations of GFAP were incubated in solution overnight at 4° C. with a known quantity of VHH until equilibrium was reached. The VHH concentration had been determined by preliminary ELISA calibrations. 100 µl of solution was transferred to a well of a microtiter plate previously coated with GFAP and was incubated for 20 min at 4° C. The plates were washed with PBS-Tween 0.1%. VHHs were detected with rabbit anti-His tag antibodies (eBiosciences, San Diego, Calif.) followed by adding β-galactosidase-conjugated goat anti-rabbit Igs (Biosys, Compiègne, France) and 4-methylumbelliferyl β-D galactoside (Sigma Aldrich, Saint-Quentin Fallavier, France). Fluorescence was read at 460 nm, after excitation at 355 nm. K$_D$ was estimated from the slope of the regression curve obtained by plotting the reciprocal of the fraction of bound antibody versus the reciprocal of the molar concentration of antigen.

Polyacrylamide Gel Electrophoresis and Western Blot

Murine brain proteins (300 mg) were extracted in a potter with 600 μl of NuPage LDS sample buffer (Invitrogen) and kept for 10 nm at 70° C. An aliquot was diluted 1:10 (v/v) with the same sample buffer then treated at 70° C. for 10 min. Following separation by polyacrylamide gel electrophoresis (PAGE) using NuPAGE Novex 4-12% Bis-tris gel (Invitrogen), semi-dry transfer onto Hybond-C (Amersham) and western blotting were carried out using the Xcell II blot module (Invitrogen). Prior to the immunochemical reaction, membranes were blocked in a 4% skimmed milk solution. Immunoblotting of membranes was accomplished with the different VHHs, and revealed by peroxidase-labeled rabbit anti-His tag (Santa Cruz, Ca, USA) followed by peroxidase labeled goat anti-rabbit immunoglobulins. Finally, peroxidase activity was visualized using a chemiluminescent kit (Amersham).

2) Results

VHHs were amplified by PCR and three successive rounds of selection were performed. After the third round of selection, DNA was purified and cloned in the pET22 vector for periplasmic expression of soluble VHHs. Twenty clones were chosen for screening by ELISA and all of these clones bind specifically to GFAP. These clones have been sequenced and three sequences, VHH-A10 (SEQ ID NO: 16), VHH-E3 (SEQ ID NO: 17) and VHH-E9 (SEQ ID NO: 18), and have been obtained. These sequences show slight differences suggesting that the specific immune response against GFAP is oligoclonal.

Yields of 1-2 mg of VHH/l of bacterial culture were obtained after immobilized metal affinity chromatography of periplasmic extracts. The single domain products were shown to be highly pure and homogenous by SDS-PAGE.

Figure 5:
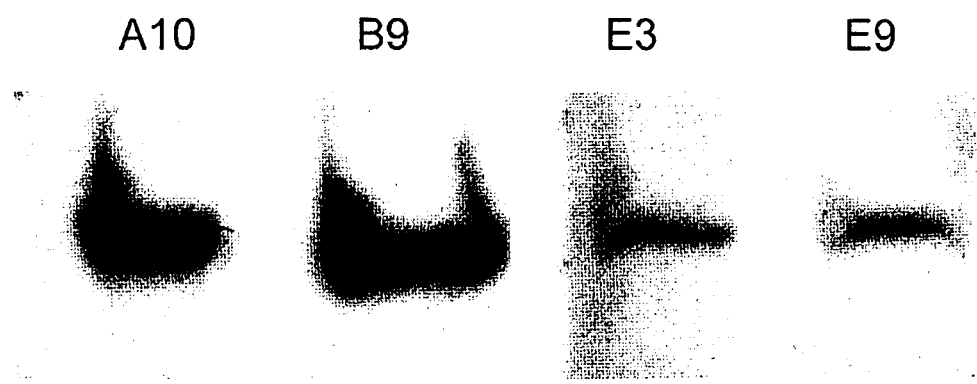
FIG. 5 shows the Western blot analyses of anti-GFAP specificities. Murine brain extracts were electrophoresed, immunoblotted and incubated with the VHH domains VHH-A10, VHH-B9, VHH-E3 and VHH-E9.

The specificity of the different VHHs was tested by ELISA and by Western blot. All the VHHs were specific for GFAP by ELISA (FIG. 5) and could detect at least 40 ng of protein. A 46 Kda band corresponding to the size of GFAP was revealed on the immunoblots of murine brain extracts (FIG. 6).

VHH-A10 and VHH-E9 has an affinity of respectively 3.1 $10^{-9}$ M and 5.6 $10^{-9}$ M while VHH-E3 affinity is in the micromolar range.

EXAMPLE 3

VHH-E9 Crosses the Blood Brain Barrier and Labels Specifically GFAP

1) Materials and Methods

Expression, Purification and Characterization of VHH-E9

The expression and purification of anti-GFAP VHH-E9 was performed according to Example 2 above. SDS-PAGE was performed using NuPAGE Novex 4-12% Bis-tris gel according to manufacturer's instructions (Invitrogen). Western blotting was performed according to Example 1 above.

Isoelectric focusing was performed using PhastSystem with PhastGel IEF 3-9. The pI Calibration Kit (Biorad) was used as standards. The pI calculation of the VHHs has been performed using EMBOSS iep software ("http://emboss.sourceforge.net/").

The heat denaturation of VHH-E9 was adapted to the method described in Olichon et al., 2007. VHHs are re-suspended in PBS/NaCl 300 mM and are heated for 15 minutes at 75° C. then cooled down at 4° C. for 20 minutes. The binding affinity of VHHs was determined by ELISA as described in Example 2 above.

Site-Directed Mutagenesis

The Quick change site directed mutagenesis kit (Stratagene) was used. The mutagenesis was performed according to manufacturer's instructions/with the following primers:

Mutations of Cysteine 22;

```
E9C22Ssens (SEQ ID NO: 19):
5'-GGGTCTCTGAGACTCTCCTCTGCAGCCTCTGG-3'

E9C22Srev (SEQ ID NO: 20):
5'-CCAGAGGCTGCAGAGGAGAGTCTCAG-3'
```

Mutations of cysteine 96
```
E9C96Ssens (SEQ ID NO: 21):
5'-CTACCTTGTTGCGTGATCGCAGAGTAATACACGGCCGT-3'

E9C96Srev (SEQ ID NO: 22):
5'-ACGGCCGTGTATTACTCTGCGATCACGCAACAAGGTAGC-3'
```

The plasmids containing the VHH were sequenced by ATGC using T7 promoter and T7 terminator primers.

Transport Across a Blood Brain Barrier In Vitro Model

Immortalized human brain endothelial cells hCMEC/D3 have been previously described in detail by Weksler et al., 2005. Cell viability in the presence of VHH was assessed by MTT assay. The permeability of hCMEC/D3 cell monolayers to VHH was measured on transwell polycarbonate insert filters (pore size 3 μm, Corning, Brumath, France). hCMEC/D3 cells were seeded on the filters at a confluent density of $2 \times 10^5$ cells/cm$^2$ in EGM-2 medium. Transport studies were performed at 3 days post-seeding. Experiments were initiated by adding VHH to the upper chamber containing either collagen, coated inserts without cells, hCMEC/D3 cells or hCMEC/D3 cells pre-exposed to various pharmacological modulators for 30 min. Transport studies were conducted at 37° C. The lower chamber was sampled at various time intervals (10, 30 and 60 min) and the presence of VHH was determined by ELISA and Western Blot.

Immunohistochemistry on Histological Sections

Adult females C57B16 mice were euthanized with sodium pentobarbital i.p. (Ceva). Brains were fixed by intra-aortic perfusion with 150 ml 4% paraformaldehyde in PBS 0.1M pH 7.4, and postfixed in the same fixative overnight at 4° C.

Vibratome sections, 70 μm in thickness, were collected in PBS 0.1M, pH 7.4. Free floating brain sections were treated to neutralize free aldehydes, endogenous peroxidases, and non-specific binding sites, prior to immunolabeling. The primary antibody VHH, diluted 1 μg/ml in PBS with 1% BSA, 1% normal goat serum, and 0.1% Triton-X100, was incubated overnight at 4° C. In the sections the VHH were decorated, successively, with rabbit anti-His tag antibodies (eBiosciences, USA) overnight at 4° C., then at room temperature with goat biotinylated anti-Rabbit IgG(H+L) (Vector BA-1000) for 2 hours, and ABC complex (Vector) for 30'. DAB was used as chromogen. Sections were collected on superfrost glass slides, dehydrated in graded ethanol solutions, and mounted in DPX neutral mounting medium (Aldrich).

Carotidian Injections of VHH In Vivo

Before intra-carotidian injections, mice were anesthetized with a single intra-peritoneal administration of a ketamine hydrochloride (Imalgen) and xylazine (Rompun) mixture.

The common carotid arteries were exposed with the aid of a microscope and canulated with fine silicon tubing (PP25× 100FT, Portex, UK). The perfusion fluid containing VHH was infused in the carotid at a constant rate by a peristaltic pump (Model PHD 2000, Harvard apparatus, Harvard, Mass.). Some animals were transiently perfused with mannitol 30%

(200 µl for 30 s) to disrupt the BBB (Rapoport et al., 1980), prior to the injection of VHH. Allowing diverse times for intra-tissular diffusion, the mice were then perfused. The presence of the VHH-His$_6$ putative intrabody in the cerebral tissue was detected using the standard immunohistochemical procedure described above.

Parasite infection: A central feature of Cerebral Malaria pathology after infection with *Plasmodium berghei* ANKA line is the alteration and opening of the BBB (Beghdadi et al., 2008). C57/B16 mice were inoculated i.p. with $10^6$ infected erythrocytes Pb ANKA per mice. At day 5 after infection, mice were injected with VHH via the carotide artery.

2) Results

Characterization of VHH-E9 (SEQ ID NO: 18)

A single 46 Kda band corresponding to the size of GFAP were revealed on the immunoblots of murine brain extracts (see FIG. 6).

The pI of VHH-E9 was determined by isoelectric focusing (IEF) (see FIG. 6) and calculated using IEP software. The pI was found to be 8.72 and 9.15, respectively for VHH-E9 with or without the His tag.

The labeling of GFAP in murine astrocytes using standard immunohistochemical procedure on free floating brain sections was analyzed. GFAP-positive astrocytes were seen mostly in the white matter, hippocampus, glia limitans, and some in the gray matter of the cerebral cortex (FIG. 7).

The affinity of VHH-E9 heated at 75° C. for 15 minutes, was measured at $3.8.10^{-9}$ M, suggesting that VHH-E9 is thermostable.

Capacity of VHH-E9 to Cross the BBB In Vitro

The capacity of VHH-E9 to cross the BBB, was tested in the in vitro BBB model developed by Weksler et al., 2005, using a monolayer of hCMEC/D3 cells. VHH-E9 was not toxic to these cells even at very high concentration (1 mg/ml). The upper chamber received 10-20 µg/ml of VHH-E9 and the rate of passage of VHH-E9 from the luminal to the abluminal side of the monolayer was measured.

FIG. 8A illustrates the transcytosis of functional VHH-E9. This time-dependent passage reaches a maximum at 30 min, and after 60 min about 1-5% of VHHs are present in the lower chamber.

Figure 9B:

It is now agreed that ionic interactions between cationic proteins and negative charges present on cell membranes trigger an adsorptive-mediated endocytosis (AME) (Vorbrodt, 1989). The contribution of AME to VHH-E9 transcytosis was then assessed. HCMEC/D3 were preincubated for 30 nm either with highly cationic protamine sulfate (40 µg/ml) or poly-lysine (300 µM), both previously shown to inhibit AME, prior to assessing VHH-E9 uptake and transport. Both cationic peptides inhibit the transendothelial migration of VHH-E9 suggesting that the transmigration is charge-dependant (FIG. 8B). To investigate whether VHH-E9 is internalized and transported by macropinocytosis, VHH transmigration was tested in the presence of 500 µM amiloride, which inhibits the formation of macropinosomes. Amiloride had an inhibitory effect on transendothelial migration of VHH-E9 (FIG. 9B).

These observations strongly suggest that VHH-E9 is transported through the endothelial cell monolayer by an intracellular endocytic mechanism rather than via inter-cellular pathway.

Capacity of VHH-E9 to Cross the BBB In Vivo

Figure 9C:
Figure 9D:
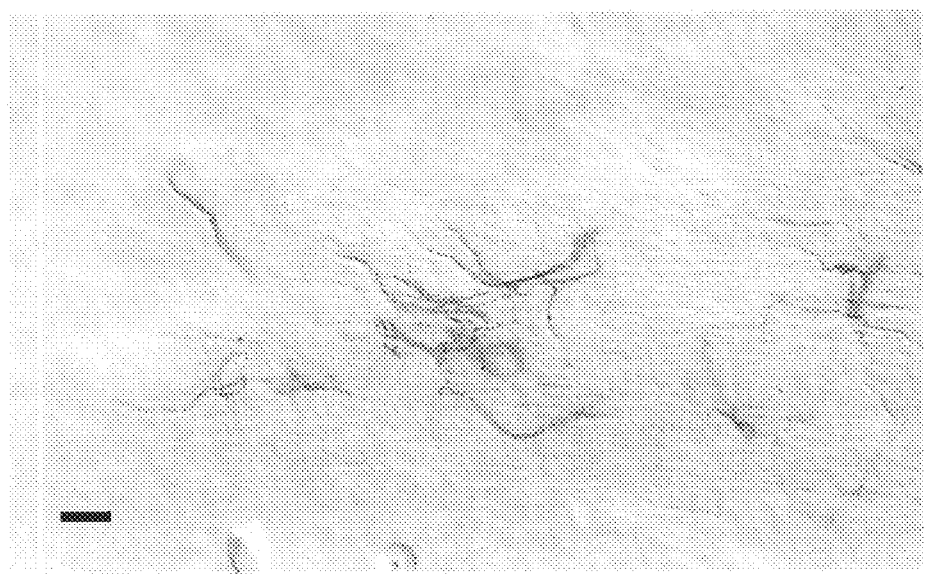
Figure 9E:

VHH-E9 was then tested in vivo for its ability to cross the BBB, in both normal and pathological conditions. Different amounts of VHH-E9 were injected via the left carotide of untreated mice, during 60 minutes. One mouse received 200 µl of VHH-E9 at the concentration of 2 mg/ml (0.4 mg); a second one received 200 µl of VHH-E9 at the concentration of 20 mg/ml (4 mg); a third one received 500 µl of VHH-E9 at the concentration of 50 mg/ml (25 mg). After the injection, the diffusion of VHH-E9 in the cerebral tissue was allowed for 1 hour before mice were euthanized and perfused with fixative. Immunostaining of astrocytes were observed only with mice that received 4 mg and 25 mg of VHH-E9 (FIG. 9). The staining pattern was similar in the 2 mice and was slightly more intense in mice receiving 25 mg of VHH. This staining was localized in astrocytic feet surrounding blood vessels, astrocytes present in the white matter (FIGS. 9 A, B), the hippocampus (FIG. 9C), pial surface (FIG. 9D), gray matter (FIG. 9E), and olfactif bulb (FIG. 9F). This staining was more intense in the left hemisphere, ipsilateral to the injected carotid, as compared to the right one (FIG. 9G). 4 mg of VHH was also injected for 60 min and mice were perfused either 90 minutes or 4 hours later. Staining was similar in the 60 and 90 min mice and reduced after 4 hours.

Pathological opening of the BBB observed in neurological (inflammatory, infectious, neoplasic) and neurodegenerative diseases, allows circulation of plasma, electrolytes, drugs, proteins, blood cells, into the cerebral tissue, with detrimental effects. The ability of VHH-E9 to go through altered BBB was investigated using either osmotic stress or cerebral malaria. The tight junctions of the cerebrovascular endothelium can be reversibly opened, in vivo, under osmotic stress. 250 µl of an hypertonic solution of mannitol 30% was injected for 30 seconds in the carotid, prior to injection of 200 µl of VHH-E9 at the concentration of 2 mg/ml, for 60 min. Significant staining of astrocytes was observed throughout the CNS (FIG. 10).

Cerebral malaria, a clinically complex syndrome of coma and encephalopathy, is correlated with the rupture of BBB integrity. In an experimental model, C57BL/6 mice developed similar neuropathological signs, five days after i.v. injection of *Plasmodium berghei* ANKA infected erythrocytes (Beghdadi et al., 2008). Intracarotidian injection of 200 µl VHH-E9 (2 mg/ml) (400 µg) during 60 min, in two infected mice, resulted in significant staining of astrocytes (FIG. 11), in the olfactive bulb (FIG. 11A), white matter (FIG. 11B), hippocampus (FIG. 11C), and the "caudal" region of the brain (FIG. 11). Again, immunostaining was more intense in the left hemisphere, ipsilateral to the VHH-E9 injected carotid, as compared to the right one (FIG. 11E). In both osmotic stress and cerebral malaria conditions, 400 µg of VHH-E9 is sufficient to label astrocytes, as compared to 4 mg needed when BBB is intact. It was then demonstrated that VHH-E9 diffuses and remains active in cerebral tissue under pathological conditions.

Characterization of VHH-E9 SS-Free

A fully functional cysteine-free derivative of VHH-E9 was generated by replacing the disulfide forming cysteine residues (Cys 22 and Cys 96) with the amino acid combination serine-serine. VHH-E9 SS-free had an affinity of $12.10^{-9}$ M, only reduced twice compared to the affinity of native VHH-E9, suggesting that the antigen binding properties were not affected by removal of disulfide bonds.

CONCLUSION

The capacity of GFAP specific-VHHs to act as transbodies and intrabodies in vitro as well as in vivo has been demonstrated. These transbodies need to fulfill a set of requirements not observed with conventional antibodies and corresponding fragments; namely: 1) they cross the BBB, 2) diffuse in brain tissues, 3) penetrate into cells, 4) are intracellularly stable, and 5) bind specifically to intracellular antigens. Once GFAP specific-VHH has penetrated into the cells, it specifically labels GFAP, suggesting that it remains active in spite of the reducing properties of the cytosol.

Antibody domains carry an internal disulfide bond, which connects both β-sheets of the β-sandwich structure and is strictly conserved during evolution, witnessing its important contribution to their stability (Alzari et al., 1988; Proba et al., 1997). Genetic removal of the disulfide bonds in the variable domains of antibody fragments (Fab, Fv or scFv) yields no functional protein, suggesting a severe loss of stability. Normal antibody fragments do not form disulfide bonds in the cytoplasm and usually are unable to achieve a stable native folding in the absence of the disulfide bonds (Biocca et al., 1995).

VHHs directed against a GFAP make them interesting agents for brain imaging and new therapeutic strategies to target intracerebral antigens such as amyloid proteins, to reach intracerebral tumor cells, or to cure infections caused by viruses, bacteria or parasites.

REFERENCES

Abulrob A. et al., *J. Neurochem.*, 2005, 95, 1201-14.
Alzari et al., *Annual Review of Immunology*, 1988, 6, 555-580
Arbabi Ghahroudi et al., *FEBS Lett.*, 1997, 414, 521-6.
Beghdadi et al., *Journal of Experimental Medicine*, 2008, 205, 395-408
Bickel U. et al., *Adv. Drug Deliv. Rev.*, 2001, 46(1-3), 247-279.
Biocca et al., *Bio/Technology*, 1995, 13, 1110-1115
Friguet et al., *J Immunol Methods*, 1985, 77, 305-319.
Girod J. et al., *J. Neurochem.*, 1999, 73: 2002-2008.
Hoogenboom and Winter, *J Mol Biol.*, 1992, 227, 381-8.
Hussain R. et al., *J. Immunol. Methods*, 1993, 160: 89-96.
Lafaye et al., *Res Immune.*, 1995, 146, 373-82; Erratum in: Res Immunol., 1996, 147, 61.
Lafaye et al., *Mol Immunol.*, 2009, 46, 695-704.
Miller D W., *J. Neurovirol.*, 1999, 5, 570-578.
Mouratou et al., *Proc Natl Acad Sci USA.*, 2007, 104, 17983-8.
Muyldermans S., *Protein Eng.*, 1994, 7, 1129-35.
Muyldermans S., *J. Biotechnol.*, 2001, 74, 277-302.
Nguyen V K. Et al., *Adv. Immunol.*, 2001, 79, 261-96.
Olichon et al. *BMC Biotechnol.*, 2007, 7, 7.
Proba et al., *Journal of Molecular Biology*, 1997, 265, 161-172
Rapoport et al., *American Journal of Physiology*, 1980, 238, R421-R431
Triguero D. et al., *Proc. Natl. Acad. Sci USA.*, 1989, 86, 4761-4765.
Triguero D. et al., *J. Pharmacol Exp Ther.*, 1991, 258: 186-192.
Vorbrodt, *Journal of Neurocytology*, 1989, 18, 359-368
Weksler B B et al., *FASEB J*, 2005, 19, 1872-4.

The invention claimed is:

1. A method of preparing a peptide vector, the method comprising:
   a) providing a variable fragment (VHH antibody) of a camelid single-chain antibody directed against an intracellular target of a human central nervous system cell (CNS), wherein said intracellular target of the human central nervous system cell is a glial fibrillary acidic protein (GFAP) protein, wherein the VHH antibody comprises or consists of the amino acid sequence of the VHH antibody included in SEQ ID NO:18; and
   b) linking the VHH antibody to a substance of interest, suitable to be delivered across the human blood-brain barrier (BBB).

2. The method of claim 1, wherein the VHH antibody comprises the amino acid sequence of the VHH antibody included in SEQ ID NO: 18.

3. The method of claim 1, wherein the substance of interest does not permeate the human blood-brain barrier.

4. The method of claim 1, wherein the substance of interest is a therapeutic or a diagnostic compound.

5. The method of claim 4, wherein the therapeutic or diagnostic compound is selected from the group consisting of a peptide, an enzyme, a nucleic acid, a virus, a fluorophore, a heavy metal chelate, a chemical entity, and a radioisotope.

6. The method of claim 1, wherein the substance of interest is a liposome or a polymeric entity comprising a therapeutic or diagnostic compound selected from the group consisting of a peptide, an enzyme, a nucleic acid, a virus, a fluorophore, a heavy metal chelate, a chemical entity, and a radioisotope.

7. The method of claim 4, wherein the therapeutic compound is present and is selected from the group consisting of an anticancer compound, an analgesic compound, an anti-inflammatory compound, an antidepressant compound, an anticonvulsant compound, and an anti-neurodegenerative compound.

8. The method of claim 4, wherein the diagnostic compound is present and is selected from the group consisting of an enzyme, a fluorophore, a heavy metal chelate, and a radioisotope.

9. The method of claim 1, wherein the VHH antibody is linked, directly or indirectly, covalently or non-covalently to the substance of interest.

10. The method of claim 1, wherein the peptide vector is able to deliver the substance of interest into the human cell comprising said intracellular target.

11. A method of targeting an intracellular target in a human central nervous system cell, comprising:
   a) providing a variable fragment (VHH antibody) of a camelid single-chain antibody directed against an intracellular target of a human central nervous system cell, wherein said intracellular target of a human central nervous system cell is a glial fibrillary acidic protein (GFAP) protein, wherein the VHH antibody comprises or consists of the amino acid sequence of the VHH antibody included in SEQ ID NO:18; and
   b) introducing into the human cell the VHH antibody.

12. The method of claim 11, wherein the VHH antibody is hyperstable.

13. The method of claim 11, wherein the human cell is an astrocyte.

14. The method of claim 1, wherein the VHH antibody selected in b) consists of the amino acid sequence of the VHH antibody included in SEQ ID NO:18.

15. A method of transporting a substance of interest across a human blood-brain barrier, the method comprising:
   a) providing a variable fragment (VHH antibody) of a camelid single-chain antibody directed against an intracellular target of a human central nervous system cell, wherein said intracellular target of a human central nervous system cell is a glial fibrillary acidic protein (GFAP) protein, wherein the VHH antibody comprises or consists of the amino acid sequence of the VHH antibody included in SEQ ID NO:18; and
   b) linking the VHH antibody to a substance of interest, to obtain a linked composition; and
   c) transporting the linked composition across the human blood-brain barrier.

16. The method of claim 1, wherein brain transendothelial migration of the VHH antibody selected in b) is inhibited in the presence of amiloride in vitro.

17. The method of claim 11, wherein the VHH antibody comprises the amino acid sequence of the VHH antibody included in SEQ ID NO:18.

18. The method of claim 15, wherein the VHH antibody comprises of the amino acid sequence of the VI-1H antibody included in SEQ ID NO:18.

19. The method of claim 15, wherein the substance of interest is a therapeutic or a diagnostic compound.

20. The method of claim 19, wherein the therapeutic or diagnostic compound is selected from the group consisting of a peptide, an enzyme, a nucleic acid, a virus, a fluorophore, a heavy metal chelate, a chemical entity, and a radioisotope.

21. The method of claim 15, wherein the substance of interest is a liposome or a polymeric entity comprising a therapeutic or diagnostic compound selected from the group consisting of a peptide, an enzyme, a nucleic acid, a virus, a fluorophore, a heavy metal chelate, a chemical entity, and a radioisotope.

22. The method of claim 19, wherein the therapeutic compound is present and is selected from the group consisting of an anticancer compound, an analgesic compound, an anti-inflammatory compound, an antidepressant compound, an anticonvulsant compound, and an anti-neurodegenerative compound.

23. The method of claim 19, wherein the diagnostic compound is present and is selected from the group consisting of an enzyme, a fluorophore, a heavy metal chelate, and a radioisotope.

24. The method of claim 15, wherein the VHH antibody is linked, directly or indirectly, covalently or non-covalently to the substance of interest.

25. The method of claim 15, wherein the peptide vector is able to deliver the substance of interest into a human cell comprising said intracellular target.

26. The method of claim 11, wherein the VHH antibody consists of the amino acid sequence of the VHH antibody included in SEQ ID NO:18.

27. The method of claim 15, wherein the VHH antibody consists of the amino acid sequence of the VHH antibody included in SEQ ID NO:18.

* * * * *